(12) United States Patent
Inaniwa et al.

(10) Patent No.: US 10,500,414 B2
(45) Date of Patent: Dec. 10, 2019

(54) IRRADIATION PLANNING APPARATUS AND IRRADIATION PLAN CORRECTION METHOD

(71) Applicant: NATIONAL INSTITUTES FOR QUANTUM AND RADIOLOGICAL SCIENCE AND TECHNOLOGY, Chiba-shi, Chiba (JP)

(72) Inventors: Taku Inaniwa, Chiba (JP); Nobuyuki Kanematsu, Chiba (JP)

(73) Assignee: National Institutes for Quantum and Radiological Science and Technology, Chiba (JP)

( * ) Notice: Subject to any disclaimer, the term of this patent is extended or adjusted under 35 U.S.C. 154(b) by 37 days.

(21) Appl. No.: 15/520,682

(22) PCT Filed: Oct. 24, 2015

(86) PCT No.: PCT/JP2015/005352
§ 371 (c)(1),
(2) Date: Apr. 20, 2017

(87) PCT Pub. No.: WO2016/063548
PCT Pub. Date: Apr. 28, 2016

(65) Prior Publication Data
US 2017/0304650 A1 Oct. 26, 2017

(30) Foreign Application Priority Data
Oct. 24, 2014 (JP) .................................. 2014-217869

(51) Int. Cl.
*A61N 5/10* (2006.01)
*A61B 6/02* (2006.01)
(Continued)

(52) U.S. Cl.
CPC .............. *A61N 5/103* (2013.01); *A61B 6/025* (2013.01); *A61B 6/032* (2013.01); *A61B 6/4014* (2013.01);
(Continued)

(58) Field of Classification Search
CPC .............................. A61B 6/582; A61B 6/583; A61N 2005/1087; A61N 2005/1061;
(Continued)

(56) References Cited

U.S. PATENT DOCUMENTS

2002/0080912 A1* 6/2002 Mackie ................ A61N 5/1048
340/1.1
2011/0220794 A1* 9/2011 Censor ................ G01N 23/046
250/307
(Continued)

FOREIGN PATENT DOCUMENTS

JP 2013/519452 A 5/2013
JP 2013-252420 A 12/2013
(Continued)

OTHER PUBLICATIONS

Palmans et al., "Calculated depth dose distributions for proton beams in some low-Z materials", Phys. Med. Biol. 42, pp. 1175-1183, 1997.
(Continued)

*Primary Examiner* — Wyatt A Stoffa
(74) *Attorney, Agent, or Firm* — Hamre, Schumann, Mueller & Larson, P.C.

(57) ABSTRACT

Provided is an irradiation planning apparatus including: a three-dimensional CT value data acquisition unit (36); a prescription data input processing unit (32) which acquires prescription data; a stopping power ratio conversion unit (37) and a nuclear reaction effective density conversion unit (38) which respectively generate first conversion data (41)
(Continued)

and second conversion data (42) on the basis of three-dimensional CT value data; and a calculation unit (33) which calculates a dose distribution on the basis of the prescription data, the first conversion data (41), and the second conversion data (42), wherein the stopping power ratio conversion unit (37) and the nuclear reaction effective density conversion unit (38) perform correction processing for correcting data obtained from the three-dimensional CT value data, using a physical quantity indicative of a likelihood of spalling particles of incident charged particle beam (3), and then determine the dose distribution. Thus, in calculation of a dose distribution in a body in particle beam irradiation planning, a dose error introduced by a difference between the probability of nuclear reaction initiated, in a body, by incident particles and the probability of nuclear reaction initiated, in water, by incident particles is simply and accurately corrected.

11 Claims, 8 Drawing Sheets

(51) Int. Cl.
*A61B 6/03* (2006.01)
*A61B 6/00* (2006.01)

(52) U.S. Cl.
CPC ............ *A61B 6/4085* (2013.01); *A61B 6/481* (2013.01); *A61N 5/1031* (2013.01); *A61N 2005/1062* (2013.01); *A61N 2005/1087* (2013.01)

(58) Field of Classification Search
CPC ............ A61N 5/103; A61N 2005/1062; A61N 5/1031; G01N 23/046; G01N 2223/419; G01T 1/2985
See application file for complete search history.

(56) References Cited

U.S. PATENT DOCUMENTS

| | | | | |
|---|---|---|---|---|
| 2012/0313002 | A1* | 12/2012 | Ikeda | A61N 5/1043 250/393 |
| 2013/0329856 | A1* | 12/2013 | Kuwahara | A61N 5/1039 378/62 |
| 2015/0199457 | A1* | 7/2015 | Brand | G06F 17/5009 703/2 |
| 2015/0352376 | A1* | 12/2015 | Wiggers | A61B 6/545 250/252.1 |
| 2018/0028143 | A1* | 2/2018 | Wiggers | A61N 5/1065 |
| 2018/0078786 | A1* | 3/2018 | Vik | A61N 5/103 |

FOREIGN PATENT DOCUMENTS

| | | |
|---|---|---|
| WO | 2011/162021 | 12/2011 |
| WO | 2012/032609 | 3/2012 |
| WO | 2012/120636 A1 | 9/2012 |

OTHER PUBLICATIONS

Schneider et al., "The water equivalence of solid materials used for dosimetry with small proton beams", Med. Phys. 29, pp. 2946-2951, 2002.

Palmans et al., "Assigning nonelastic nuclear interaction cross sections to Hounsfield units for Monte Carlo treatment planning of proton beams", Phys. Med. Biol. 50, pp. 991-1000, 2005.

Al-Sulaiti et al., "Water equivalence of various materials for clinical proton dosimetry by experiment and Monte Carlo simulation", Nucl. Instrum. Meth. A 619, pp. 344-347, 2010.

International Search Report and Written Opinion, International Patent Application No. PCT/JP2015/005352, dated Jan. 12, 2016, with English translation (12 pages).

* cited by examiner

IRRADIATION PLANNING APPARATUS AND IRRADIATION PLAN CORRECTION METHOD

TECHNICAL FIELD

The present invention relates to an irradiation planning apparatus, an irradiation planning program, an irradiation plan correction program, and an irradiation plan correction method, each for, for example, developing a particle beam irradiation plan.

BACKGROUND ART

Conventionally, an irradiation planning apparatus for use in particle beam therapy, typified by proton beam therapy and carbon ion therapy, assumes a human body approximately to be water having a different density, and applies a dose distribution obtained by a measurement in water to a human body, which is an inhomogeneous medium, to calculate a dose distribution in a body (see Patent Literature 1). In practice, by using a conversion table previously prepared for each CT apparatus and for each imaging condition, pixel values of a CT image (CT values) of a patient are converted into a stopping power ratio that represents an effective density of a material for a particle beam, and thus a human body is expressed as water having a different density. Here, a CT value represents an effective radiation source attenuation coefficient of a material with respect to an X-ray.

However, a human tissue differs from water. Therefore, a rate of nuclear reaction initiated, in a body, by incident particles differs from a rate of nuclear reaction initiated, in water, by incident particles. The existence of a difference between these rates of nuclear reaction means that the number of the incident particles reaching almost the end of stopping range differs between in a body and in water.

Here, the proportion of the incident particles that reach almost the stopping location has a direct effect on the height of a Bragg peak. Therefore, an error due to a difference between nuclear reaction in water and in a body occurs in the dose distribution of an irradiation plan that has been developed by applying, to a human body, a dose distribution obtained by a measurement in water. In addition, the magnitude of this error varies from patient to patient and depending on the beam direction.

However, no practical algorithms have yet been reported that correct this error.

Meanwhile, absolute dose measurement performed for quality assurance often uses a solid phantom, due to easy handling, as a substitute for water, which is a standard material. In this case, it is reported that a dose error occurs from a difference in composition (hence, a difference in the probability of nuclear reaction) between water and a solid phantom (see Non-Patent Literatures 1 and 2).

In order to correct this dose error, absolute dose measurement is performed such that a factor for converting a measured value in a solid phantom into a value that would be measured in water (fluence correction factor) is initially determined by using Monte Carlo calculation, or on the basis of actual measured data. Using this factor, measured values in a solid phantom are converted into dose values in water (Non-Patent Literatures 3 and 4).

Ideally, a dose error occurring in calculation of a dose distribution in a patient body can also be corrected using a fluence correction factor.

However, measuring the correction factor in an actual patient body is not possible. In addition, calculation of a correction factor for each patient and for each beam by using Monte Carlo calculation is impractical as well.

CITATION LIST

Patent Literature

Patent Literature 1: JP 2013-252420 A

Non-patent Literature

Non-Patent Literature 1: Palmans H and Verhaegen F, 1997, Calculated depth dose distributions for proton beams in some low-Z materials, Phys. Med. Biol. 42, 1175-83

Non-Patent Literature 2: Schneider U, Pemler P, Besserer J, Dellert M, Moosburger M, Boer J, Pedroni E and Boehringer T, 2002, The water equivalence of solid materials used for dosimetry with small proton beams, Med. Phys. 29, 2946-51

Non-Patent Literature 3: Palmans H and Verhaegen F, 2005, Assigning nonelastic nuclear interaction cross sections to Hounsfield units for Monte Carlo treatment planning of proton beams, Phys. Med. Biol. 50, 991-1000

Non-Patent Literature 4: Al-Sulaiti L, Shipley D, Thomas R, Kackperek A, Regan P and Palmans H, 2010, Water equivalence of various materials for clinical proton dosimetry by experiment and Monte Carlo simulation, Nucl. Instrum. Meth. A 619, 344-7

SUMMARY OF THE INVENTION

Technical Problems

In view of the foregoing problems, it is an object of the present invention to provide an irradiation planning apparatus, an irradiation planning program, an irradiation plan correction program, and an irradiation plan correction method that, in calculation of a dose distribution in a body in particle beam irradiation planning, each correct simply and accurately a dose error introduced by a difference between the probability of nuclear reaction initiated, in a body, by incident particles, and the probability of nuclear reaction initiated, in water, by incident particles.

Solution to Problems

The present invention is directed to an irradiation planning apparatus for developing an irradiation plan involving a particle beam, including a three-dimensional scanned data acquisition unit that acquires three-dimensional scanned data generated by three-dimensional scanning of an object to be irradiated (hereinafter referred to as irradiated object) of the particle beam by means of a radiation different from the particle beam, a prescription data acquisition unit that acquires prescription data indicative of a position and a volume of a region irradiated with the particle beam for the irradiated object, a reaction-physical-quantity distribution data generation unit that generates reaction physical quantity distribution data indicative of a distribution of a physical quantity indicative of capability, of a material of the irradiated object, of reacting with the particle beam on the basis of the three-dimensional scanned data, and a dose distribution calculation unit that calculates a dose distribution on the basis of the prescription data and the reaction physical quantity distribution data, wherein the reaction-physicalquantity distribution data generation unit includes a stopping power ratio correction processing unit that converts the three-dimensional scanned data into a stopping power ratio, which is a physical quantity indicative of capability of decelerating incident particles, of a material of interest, relative to corresponding capability of water, and generates three-dimensional stopping power ratio data, and an irradiated object material correction processing unit that determines, from the three-dimensional stopping power ratio data, a correction factor representing a difference between in water and in an irradiated object material, and performs correction, depending on depth, of a depth dose distribution of the particle beam using the correction factor. The present invention is also directed to an irradiation planning program, an irradiation plan correction program, and an irradiation plan correction method, each for use in or with the irradiation planning apparatus.

Advantageous Effects of Invention

The present invention can provide an irradiation planning apparatus, an irradiation planning program, an irradiation plan correction program, and an irradiation plan correction method that, in calculation of a dose distribution in a body in particle beam irradiation planning, each correct simply and accurately a dose error introduced by a difference between the probability of nuclear reaction initiated, in a body, by incident particles, and the probability of nuclear reaction initiated, in water, by incident particles.

DESCRIPTION OF EMBODIMENTS

The present inventors have made intensive studies to eliminate, in calculation of a dose distribution in a body in particle beam irradiation planning, a dose error introduced by a difference between the probability of nuclear reaction initiated, in a body, by incident particles, and the probability of nuclear reaction initiated, in water, by incident particles.

The present inventors have thus developed a method for correcting this dose error simply and accurately. A fundamental principle of this correction method will be described first.

<In Carbon Ion Therapy>

In carbon ion therapy, as a carbon ion beam penetrates into a body, the number of carbon ions decreases via nuclear spallation reaction of a proportion of the carbon ions with atomic nuclei in the body. On the contrary, the number of fragments generated during the nuclear spallation reaction gradually increases, and these fragments widely spread even beyond the stopping location of the carbon ion beam.

Figure 1:
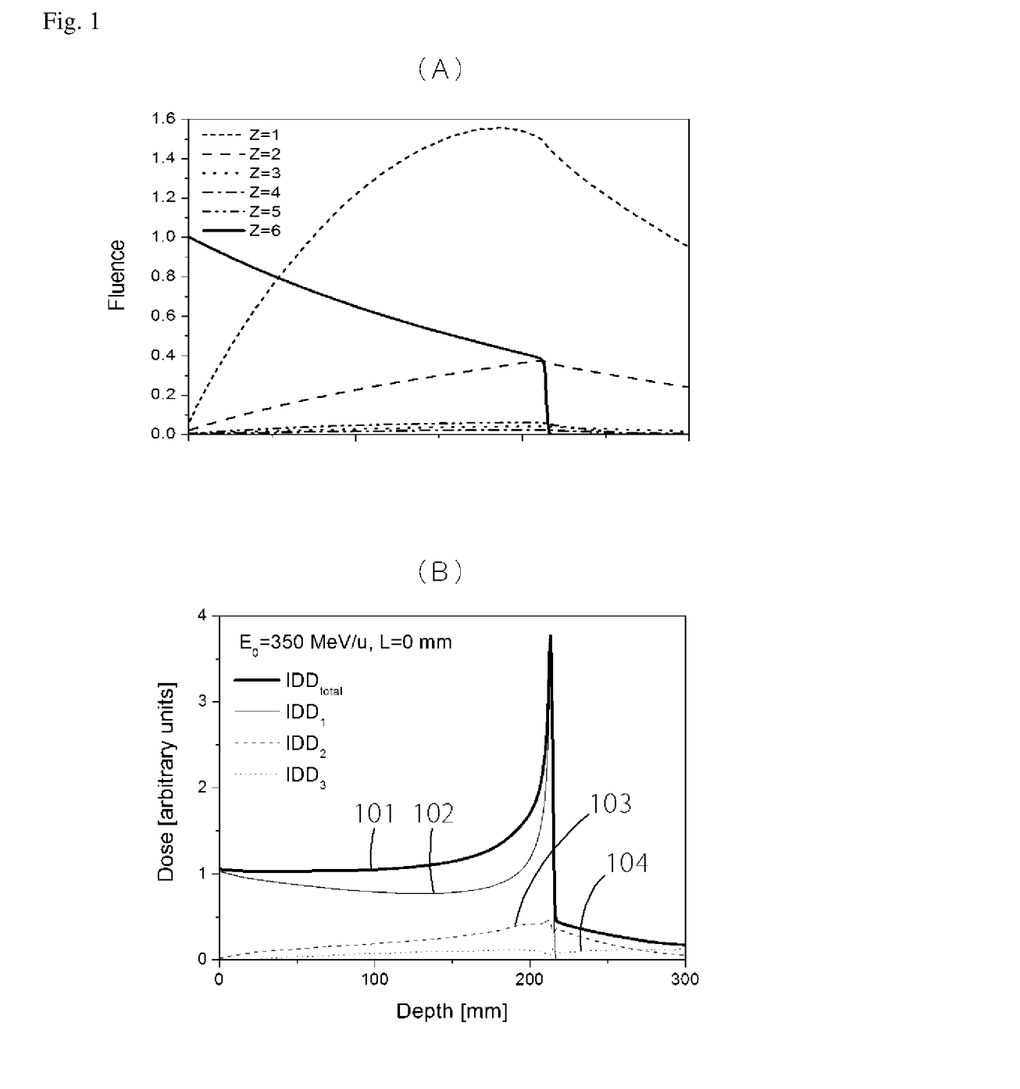
FIG. 1 is an illustrative diagram including graphs that show doses.

FIG. 1(A) is a diagram illustrating depth number-of-particles distributions of a carbon ion beam in water for the respective atomic numbers obtained by Monte Carlo calculation. The horizontal axis represents the depth from the body surface, and the vertical axis represents the fluence. A dose distribution $d_j(x, y, z)$ of a carbon ion beam is accounted for by dose contributions of the incident particles (carbon ions) and of the fragments, and can thus be represented by Equation (Eq.) 1 shown below as a superposition of three components in view of differences in spreading along a transverse direction.

$$d_j(x, y, z) = \sum_{n=1}^{3} d_{n,j}(x, y, z) = \sum_{n=1}^{3} [I_n(s_S(z), E_{0j}, L_j) \cdot G(x, y, \sigma_{n,j}(z))] \quad \text{Eq. 1}$$

where:

$d_{n,j}(x, y, z)$ represents a dose distribution of an n-th component;

$I_n$ represents a depth dose distribution (integrated depth dose (IDD)) obtained by integrating the dose distribution of the n-th component over a plane perpendicular to the beam axis; and $G(x, y, \sigma_{n,j}(z))$ represents a two-dimensional normal distribution having a standard deviation $\sigma$.

For more detail, see Inaniwa T, Furukawa T, Nagano A, Sato S, Saotome N, Noda K and Kanai T, 2009, Field-size effect of physical doses in carbon-ion scanning using range shifter plates, Med. Phys. 36, 2889-97.

Here, an approximation is made such that the first component (first domain) describes a contribution of the incident particles (e.g., carbon ions in carbon ion therapy); the second component (second domain) describes a contribution of heavier fragments other than fragments having atomic numbers 1 and 2; and the third component (third domain) describes a contribution of lighter fragments having atomic numbers of 1 and 2.

FIG. 1(B) is a graph chart showing, by way of example, a depth dose distribution of a carbon ion beam having energy of 290 MeV/u. The horizontal axis represents the depth from the body surface, and the vertical axis represents the dose. The graph 101 represents the depth dose distribution $IDD_{total}$ in water of the carbon ion beam. The graph 102 represents the dose contribution of the first component (Z=6). The graph 103 represents the dose contribution of the second component (Z=3 to 5). The graph 104 represents the dose contribution of the third component (Z=1 to 2).

In a particle beam irradiation plan, pixel values of a CT image (CT values) of a patient are converted into a stopping power ratio $\rho_S$ of a material with respect to water using a previously prepared conversion table, and thus a human body, which is an inhomogeneous medium, is represented in a form of distribution of stopping power ratio. Here, the stopping power ratio $\rho_S$ is a physical quantity indicative of capability of decelerating incident particles, of a material of interest, relative to corresponding capability of water. In a particle beam irradiation plan, in general, a dose distribution in a body is calculated by applying a dose distribution obtained by a measurement in water, such as one shown in FIG. 1(B), to the distribution of stopping power ratio obtained by the conversion.

The present inventors have derived a universal correlation of the stopping power ratio $\rho_S$ with a nuclear reaction effective density $\rho_N$ for each tissue on the basis of the composition list of human tissues compiled in an ICRU report (ICRU Report 1992). Here, the nuclear reaction effective density $\rho_N$ is a physical quantity indicative of a likelihood of spalling incident particles, of a material of interest, relative to a corresponding likelihood of water.

In the present invention, a three-dimensional distribution of the stopping power ratio $\rho_S$ is first determined from the three-dimensional distribution of CT values obtained by three-dimensional scanning performed by a CT apparatus using an X-ray, which is a radiation different from the particle beam. Then, using a correlation between $\rho_S$ and $\rho_N$, a three-dimensional distribution of the nuclear reaction effective density $\rho_N$ is generated.

An effective distance $S_S(z)$ from the body surface to a depth of interest z in association with deceleration of particles can be obtained by line integration of the stopping power ratio $\rho_S$ to the depth of interest z, as given by Eq. 2 shown below.

$$S_S(z) = \int_0^z \rho_S(z') dz' \quad \text{Eq. 2}$$

Meanwhile, an effective distance $S_N(z)$ to the depth z in association with spallation of particles (i.e., initiation of nuclear reaction) can be obtained by line integration of the nuclear reaction effective density $\rho_N$ to the depth z, as given by Eq. 3 shown below.

$$S_N(z) = \int_0^z \rho_N(z') dz' \quad \text{Eq. 3}$$

In this regard, Haettner et al. have conducted an experiment to measure particle flux (fluence) of carbon ion beams in water (for more detail, see Haettner E, Iwase H, Kramer M, Kraft G and Schardt D, 2013, Experimental study of nuclear fragmentation of 200 and 400 MeV/u 12C ions in water for applications in particle therapy, Phys. Med. Biol. 58, 8265-79).

Using an exponential decay model of carbon ion beam fluence, Kanematsu et al. have determined that the mean free path λ of a carbon ion beam is 255 mm (for more detail, see Kanematsu N, Koba Y and Ogata R, 2013, Evaluation of plastic materials for range shifting, range compensation, and solid phantom dosimetry in carbon-ion radiotherapy, Med. Phys. 40, 041724-1-6).

Using this relationship, the deviation in carbon ion beam fluence caused by nuclear reaction in water and in a body before the carbon ion beam reaches a depth of interest z can be represented by Eq. 4 shown below.

$$\phi_w^P(z) = \frac{\exp\left(-\frac{S_N(z)}{\lambda}\right)}{\exp\left(-\frac{S_S(z)}{\lambda}\right)} = \exp\left(\frac{S_S(z) - S_N(z)}{\lambda}\right) \quad \text{Eq. 4}$$

where $\varphi_w^P(z)$ is herein referred to as attenuation correction factor.

If a carbon ion beam travels through a material having a ratio of the probability of nuclear reaction relative to the stopping power higher than a corresponding ratio of water, a relationship of $S_S(z) < S_N(z)$ holds, and thus the attenuation correction factor satisfies, by definition, a relationship of $\varphi_w^P(z) < 1.0$.

Conversely, if a carbon ion beam travels through a material having a ratio of the probability of nuclear reaction relative to the stopping power lower than a corresponding ratio of water, a relationship of $S_S(z) > S_N(z)$ holds, and thus the attenuation correction factor satisfies a relationship of $\varphi_w^P(z) > 1.0$.

Using this correction factor, the equation for correcting a depth dose distribution shown by Eq. 1 can be rewritten as Eq. 5 shown below.

$$d'_j(x, y, z) = \sum_{n=1}^{3} d'_{n,j}(x, y, z) \quad \text{Eq. 5}$$

$$= \phi_w^P \cdot I_{1,j} \cdot G_{1,j} + I_{2,j} \cdot G_{2,j} + \frac{1}{\phi_w^P} \cdot I_{3,j} \cdot G_{3,j}$$

A dose of incident particles is proportional to the fluence of those incident particles, and therefore, $I_{1,j}$ is corrected by a factor of $\varphi_w^P(z)$. The number of fragments increases with an increase in the degree of attenuation of incident particles, and therefore, the dose contribution of the third component $I_{3,j}$ is corrected by a factor of $\varphi_w^P(z)$. The dose contribution of the second component $I_{2,j}$ is not corrected, empirically.

Figure 2:
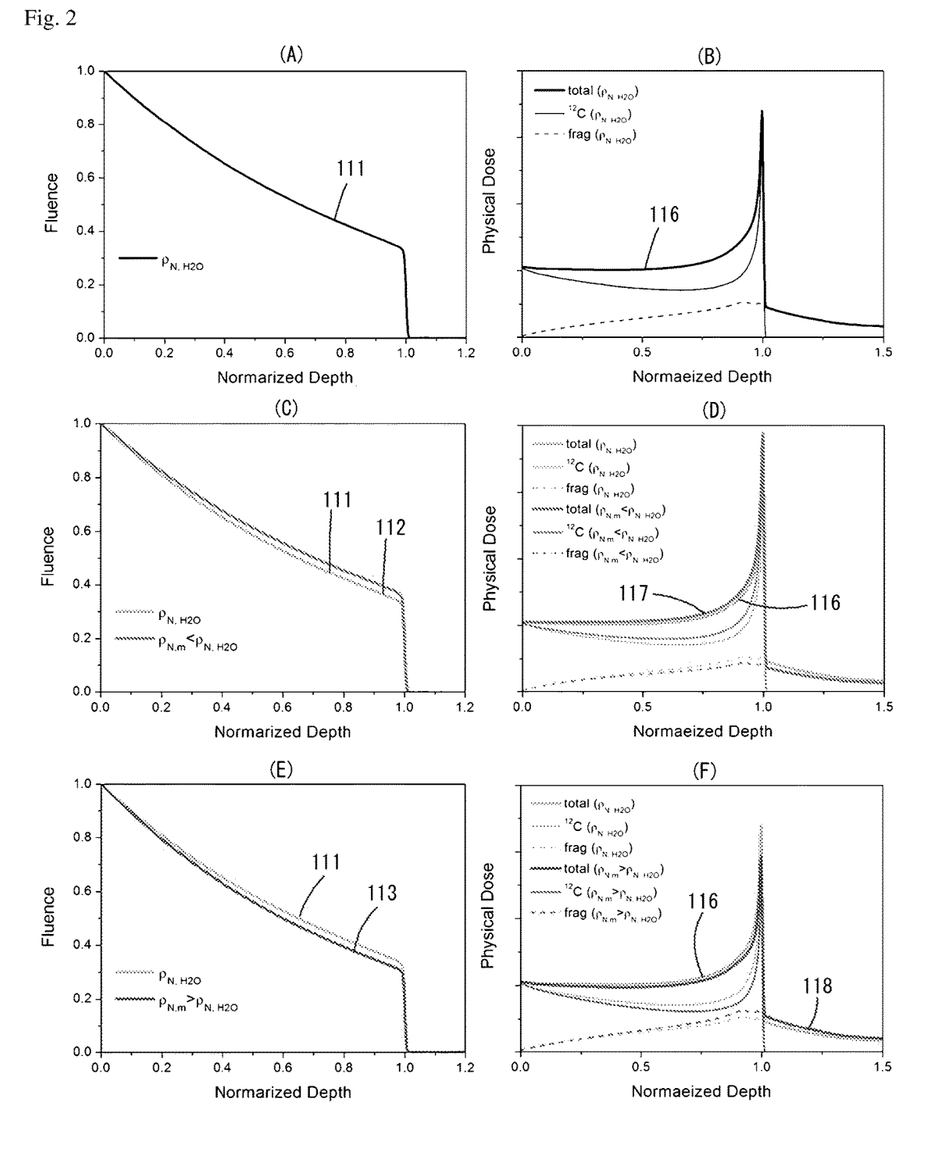
FIG. 2 is an illustrative diagram including graphs that schematically show the dose distribution correction.

FIG. 2 is an illustrative diagram using graphs that schematically show the dose distribution correction. FIGS. 2(A), 2(C), and 2(E) each have a vertical axis representing the carbon ion beam fluence, and a horizontal axis representing the depth from the body surface. FIGS. 2(B), 2(D), and 2(F) each illustrate a Bragg curve, and each have a vertical axis representing the depth dose, and a horizontal axis representing the depth from the body surface.

FIGS. 2(A) and 2(B) respectively illustrate the carbon ion beam fluence and the depth dose, both in water. As shown, the graph 111 shows the carbon ion beam fluence as being decreasing with the depth, and the graph 116 shows a peak occurring near the depth of 1.0.

FIGS. 2(C) and 2(D) respectively illustrate the carbon ion beam fluence and the depth dose, both in a material having a ratio of the likelihood of nuclear reaction relative to the stopping power lower than a corresponding ratio of water ($\varphi_w^P(z) > 1.0$). As shown, the graph 112 lies slightly above the graph 111 over the entire range in general, and the graph 117 lies also slightly above the graph 116 over the entire range in general.

FIGS. 2(E) and 2(F) respectively illustrate the carbon ion beam fluence and the depth dose, both in a material having a ratio of the likelihood of nuclear reaction relative to the stopping power higher than a corresponding ratio of water ($\varphi_w^P(z) < 1.0$). As shown, the graph 113 lies slightly below the graph 111 over the entire range in general, and the graph 118 lies also slightly below the graph 116 over the entire range in general. Thus, a material more likely to undergo nuclear reaction reduces the fluence and the depth dose, while a material less likely to undergo nuclear reaction increases the fluence and the depth dose.

Figure 3:
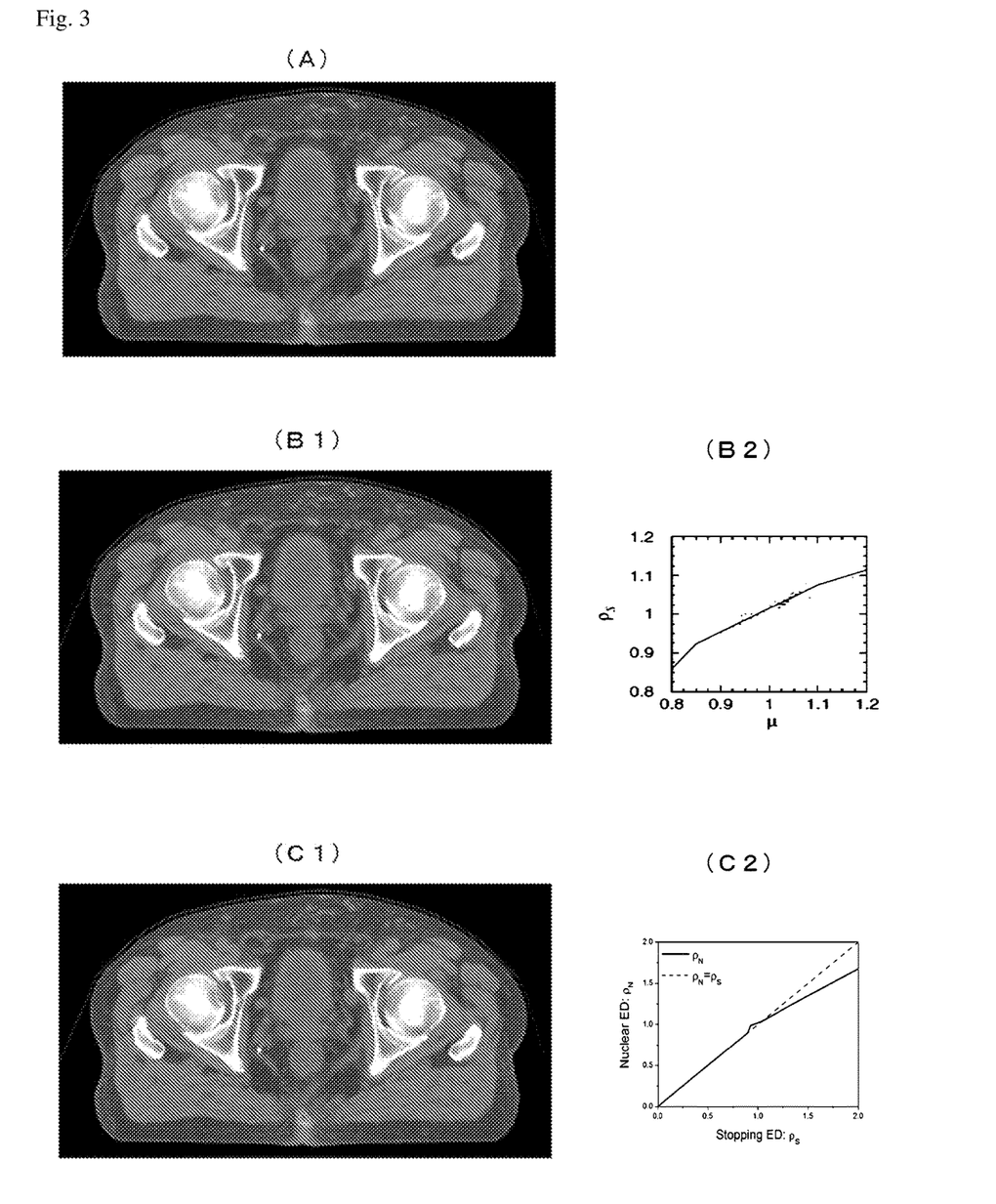
FIG. 3 is an illustrative diagram including an image of three-dimensional scanned data together with images after conversion.

FIG. 3 is an image diagram illustrating a series of conversion. FIG. 3(A) shows an image of CT values obtained using an attenuation coefficient μ. FIG. 3(B1) shows an image related to stopping power ratio (stopping power ratio image), obtained after correction using a stopping power ratio $\rho_S$. FIG. 3(C1) shows an image related to nuclear reaction effective density (nuclear reaction effective density image), obtained after further correction using a nuclear reaction effective density $\rho_N$. FIG. 3(B2) has a vertical axis representing the stopping power ratio, and a horizontal axis representing the attenuation coefficient, and illustrates the conversion table for use in generating the stopping power ratio image from the image of CT values. FIG. 3(C2) has a vertical axis representing the nuclear reaction effective density, and a horizontal axis representing the stopping power ratio, and illustrates the conversion table for use in generating the nuclear reaction effective density image from the stopping power ratio image. Thus, generation of a nuclear reaction effective density image from CT values to apply the corrections described above enables an accurate particle beam irradiation plan to be developed.

<In Proton Beam Therapy>

A proton beam traveling in water undergoes, with electrons or atomic nuclei in water molecules, electromagnetic interaction (EM), in which the proton beam loses energy and decelerates, providing energy to electrons in water molecules (or in a body, electrons in the body); elastic interaction (EL), in which energy is provided while the total kinetic energy is conserved, and the type of the atomic nuclei does not change; inelastic interaction (IE), in which energy is provided while the type of the atomic nuclei does not change, but the atomic nuclei are excited; and nuclear reaction (nonelastic interaction: NE), which is the reaction other than the reactions described above (i.e., other than EM, EL, and IE). Note that a proton that undergoes EL or IE loses a small amount of energy during that reaction, but reaches a depth that is almost the same as that of a proton flux that undergoes only EM. Collectively treating the proton fluxes that undergo EL and IE in a same manner allows the dose distribution D(s) of the dose provided by a proton beam to water to be represented by summation of contributions of the respective types of interaction ($D_{EM}(s)$, $D_{EL/IE}(s)$, and $D_{NE}(s)$), as shown by Eq. 6 shown below.

$$D(s)=D_{EM}(s)+D_{EL/IE}(s)+D_{NE}(s) \quad \text{Eq. 6}$$

where $D_{EM}(s)$ represents an absorbed dose to water with respect to incident particles that have undergone only EM interaction;

$D_{EL/IE}(s)$ represents an absorbed dose to water with respect to incident particles that have undergone EL interaction or IE interaction; and $D_{NE}(s)$ represents an absorbed dose to water caused by NE interaction.

Meanwhile, when a proton flux travels in a material other than water, a dose provided to the material (dose to water in material) at a depth z in that material (water equivalent depth s) is represented by Eq. 7 shown below.

$$D(z) = \frac{1-A's(z)}{1-As(z)} D_{EM}(s(z)) + \frac{Y'}{Y} D_{ELAE}(s(z)) + \frac{\gamma'}{\gamma} \frac{(A'-Y')}{(A-Y)} D_{NE}(s(z)) \quad \text{Eq. 7}$$

Each of the components (terms) in Eq. 7 will now be described below.

<First Component: EM-Related Part>

The element 1—As represents a change in the number of the protons (fluence) that have undergone only EM interaction in water. The coefficient A represents the slope, and 1—As thus represents the degree of reduction in the number of the protons (fluence) that have undergone only EM interaction at the depth s in water.

The element 1−A's represents a reduction in fluence at the same depth as the depth in water in a material other than water.

That is, the ratio (1−A's)/(1−As) provides correction in relation to how much the level of EM reaction differs from that in water at the depth s.

<Second Component: EL/IE-Related Part>

The coefficient Y represents the slope, and thus represents the degree of increase in the number of the protons (fluence) that have undergone EL interaction or IE interaction at the depth s in water.

The coefficient Y' represents the degree of increase in the number of the protons (fluence) that have undergone EL interaction or IE interaction at the same depth as the depth in water in a material other than water.

That is, the ratio Y'/Y provides correction in relation to how much the level of EL and IE reactions differs from that in water at the depth s. Note that, although Y'/Y may be inherently represented as Y's/Ys, the depths s in the numerator and in the denominator are canceled out, and accordingly, the expression Y'/Y is used.

<Third Component: NE-Related Part>

The element A−Y represents the level of NE reaction in water.

The element A'−Y' represents the level of NE reaction at a same depth as the depth in water (water equivalent depth) in the material.

That is, the ratio A'−Y'/A−Y provides correction in relation to how much the level of NE reaction in the material differs from that in water at the water equivalent depth s.

The coefficient γ represents the amount of energy provided to a charged particle when an incident proton undergoes nuclear reaction in water. In more detail, a charged particle produced by nuclear reaction provides energy in the vicinity of where that nuclear reaction has occurred, and thus the amount of this energy is taken into consideration in the dose calculation, while, in contrast, a neutron and/or gamma ray produced by nuclear reaction does not provide much energy in the vicinity of where that nuclear reaction has occurred, and thus the amount of this energy is not taken into consideration in the dose calculation. Thus, a high γ value indicates that a larger portion of energy is provided to charged particles, while a low γ value indicates that a larger portion of energy is provided to neutrons and/or gamma rays, and that a smaller portion of energy is provided to charged particles.

The coefficient γ' represents the level of nuclear reaction and the amount of energy provided to a charged particle by a material other than water.

That is, the ratio γ'/γ represents how much the proportion of energy provided to charged particles differs from that in water at the depth s upon NE reaction.

Here, the correction factor (1−A's(z))/(1−As(z)) for $D_{EM}$ represents the ratio of the number of the primary protons that undergo only EM interaction in the material relative to the corresponding number in water; and the correction factor Y'/Y for $D_{EL/IE}$ represents the ratio of the number of the protons that undergo EL/IE interaction in the material relative to the corresponding number in water.

In addition, the correction factors γ'/γ and (A'−Y')/(A−Y) for $D_{NE}$ represent the ratio of "the proportion of the energy of the protons that have undergone nuclear reaction to the energy provided to the target charged particles" in the material relative to the corresponding proportion in water; and the ratio of "the number of the protons that undergo nuclear reaction" in the material relative to the corresponding number in water, respectively. If physical properties of the material change continuously with the depth z, then Eq. 7 provided above can be rewritten as Eq. 8 shown below without loss of generality.

$$D(z) = \frac{\left(1 - \int_0^z A'(\hat{z})\rho_s(\hat{z})d\hat{z}\right)}{1 - As(z)} D_{EM}(s(z)) +$$

$$\frac{\int_0^z Y'(\hat{z})\rho_s(\hat{z})d\hat{z}}{Y_s(z)} D_{ELAE}(s(z)) + \frac{\gamma'(z)}{\gamma} \frac{(A'(z) - Y'(z))}{(A - Y)} D_{NE}(s(z))$$

Eq. 8

That is, if the correction factors A, A', Y, Y', and γ'/γ and the stopping power ratio $\rho_S$ are known for each material, then correcting the dose contributions $D_{EM}$, $D_{EL/IE}$, and $D_{NE}$ of the respective types of interaction in water, and summing up the corrected dose contributions according to Eq. 8 enables the dose distributions in that material to be calculated.

Figure 4:
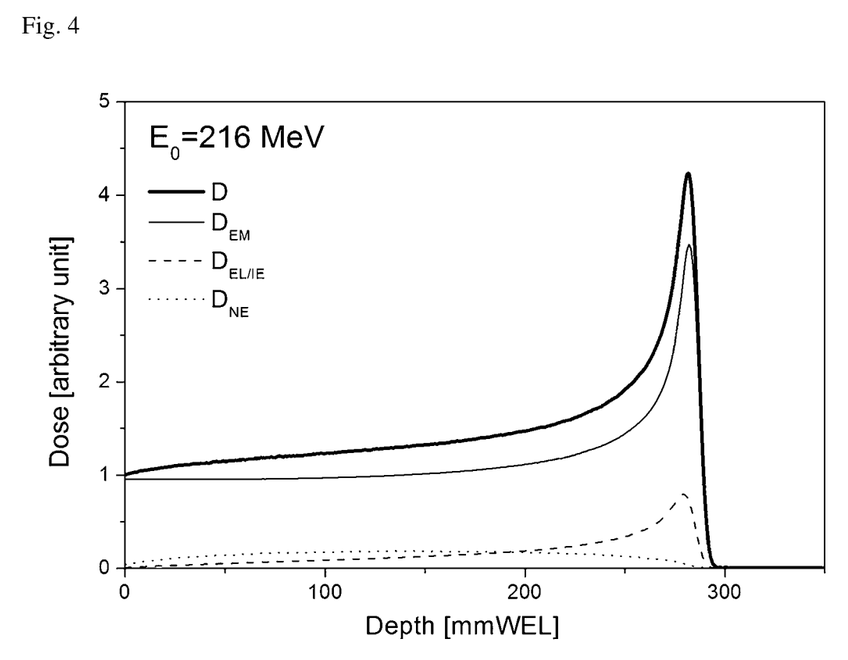
FIG. 4 is a graph chart showing a depth dose distribution and contributions of respective types of interaction in water of a proton beam.

FIG. 4 is a graph chart showing a depth dose distribution D and contributions $D_{EM}$, $D_{EL/IE}$, and $D_{NE}$ of the respective types of interaction in water, of a proton beam having energy of 216 MeV. The vertical axis represents the dose, and the horizontal axis represents the depth.

In a particle beam irradiation plan, pixel values of a CT image (CT values) of a patient are converted into a stopping power ratio $\rho_S$ of a material with respect to water using a previously prepared conversion table, and thus a human body, which is an inhomogeneous medium, is represented in a form of distribution of stopping power ratio. Here, the stopping power ratio $\rho_S$ is a physical quantity indicative of capability of decelerating incident particles, of a material of interest, relative to corresponding capability of water. In a particle beam irradiation plan, in general, a dose distribution in a body is calculated by applying a dose distribution obtained by a measurement in water to the distribution of stopping power ratio obtained by the conversion.

The present inventors have created a human tissue phantom in a Monte Carlo simulation code GEANT 4 to simulate proton beam irradiation onto the phantom on the basis of the composition list of human tissues compiled in an ICRU report (ICRU Report 1992), and thus derived universal correlations of the stopping power ratio $\rho_S$ with correction factors A'/A, Y'/Y, and γ'/γ for each tissue. The EM attenuation coefficient A and the EL/IE yield Y for water, which is a reference material, have also been determined by simulating proton beam irradiation using GEANT 4.

Figure 5:
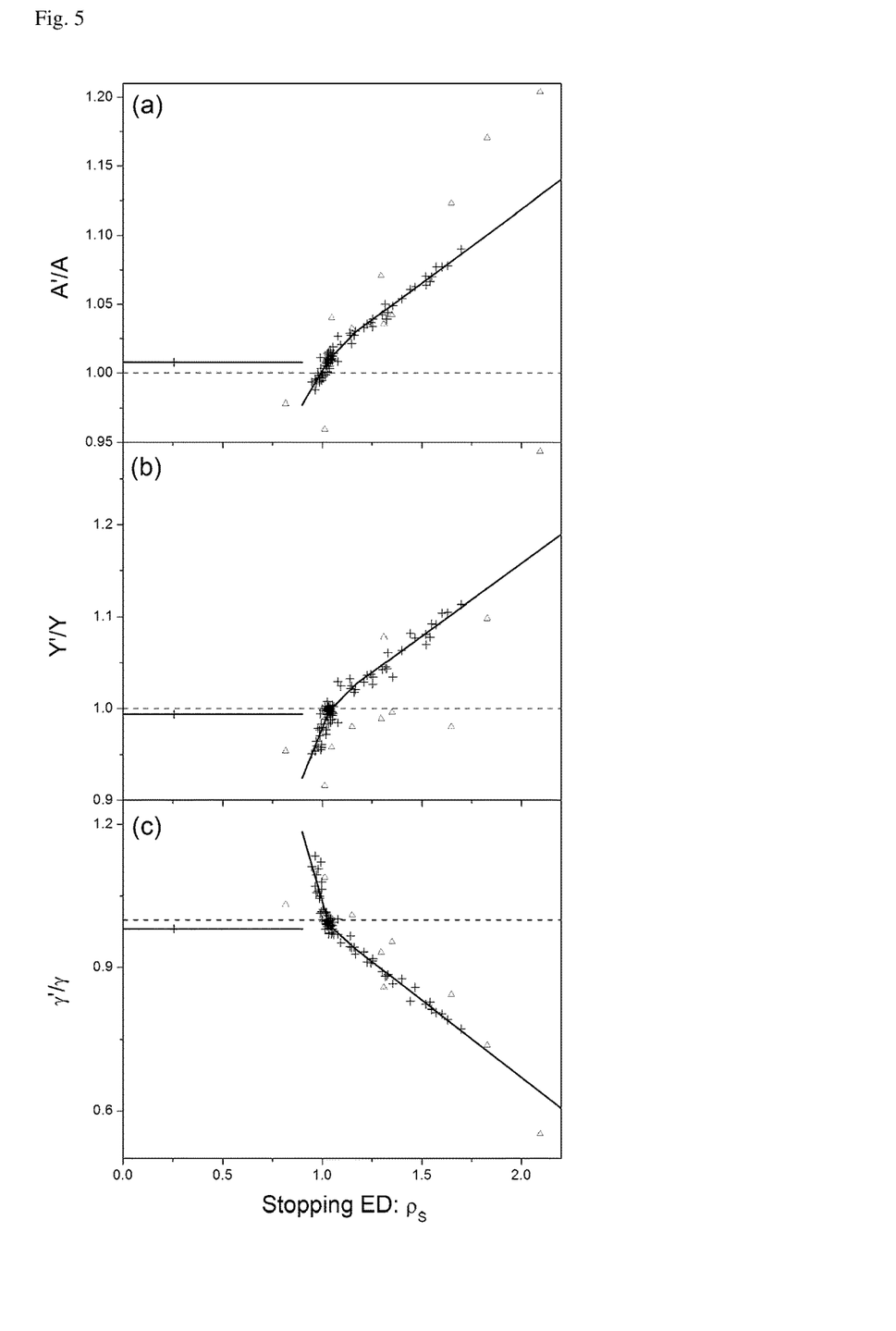
FIG. 5 is an illustrative diagram showing relationships between stopping power ratios of ICRU human tissues and correction factors.

FIG. 5 is an illustrative diagram showing relationships between the stopping power ratio $\rho_S$ of ICRU human tissues and correction factors A'/A, Y'/Y, and γ'/γ. In each graph, the vertical axis represents the correction factor, and the horizontal axis represents the stopping power ratio (likelihood of stopping a particle beam). The positive signs (+) in the graphs are what have been plotted for each value of parameters for each tissue (material) picked up from the ICRU human tissues data. In each graph, a stopping power ratio greater than 1.0 indicates that the tissue (material) is more likely to stop a particle beam than water, while, in contrast, a stopping power ratio less than 1.0 indicates that the tissue (material) is less likely to stop a particle beam than water.

FIG. 5(a) is a graph of the correction factor A'/A for EM interaction. FIG. 5(b) is a graph of the correction factor Y'/Y for EL/IE interaction. FIG. 5(c) is a graph of the correction factor A'/A for NE interaction. As shown, the graphs of the correction factors show a positive correlation for EM and for EL/IE in FIGS. 5(a) and 5(b), and a negative correlation for NE in FIG. 5(c).

In a particle beam therapy planning apparatus, a CT value representing an effective linear attenuation coefficient for an X-ray is converted into a stopping power ratio $\rho_S$ through a conversion table (each calibrated for the specific CT apparatus and specific imaging conditions). That is, in a therapy planning apparatus, the stopping power ratio distribution $\rho_S$ in a patient body is previously determined for performing dose calculation. This allows application of the correction of Eq. 8 to dose calculation for a body using the universal correlations of the stopping power ratios $\rho_S$ with the correction factors A'/A, Y'/Y, and γ'/γ shown in FIG. 5, as well as using the EM attenuation coefficient A and the EL/IE yield Y of water.

Figure 6:
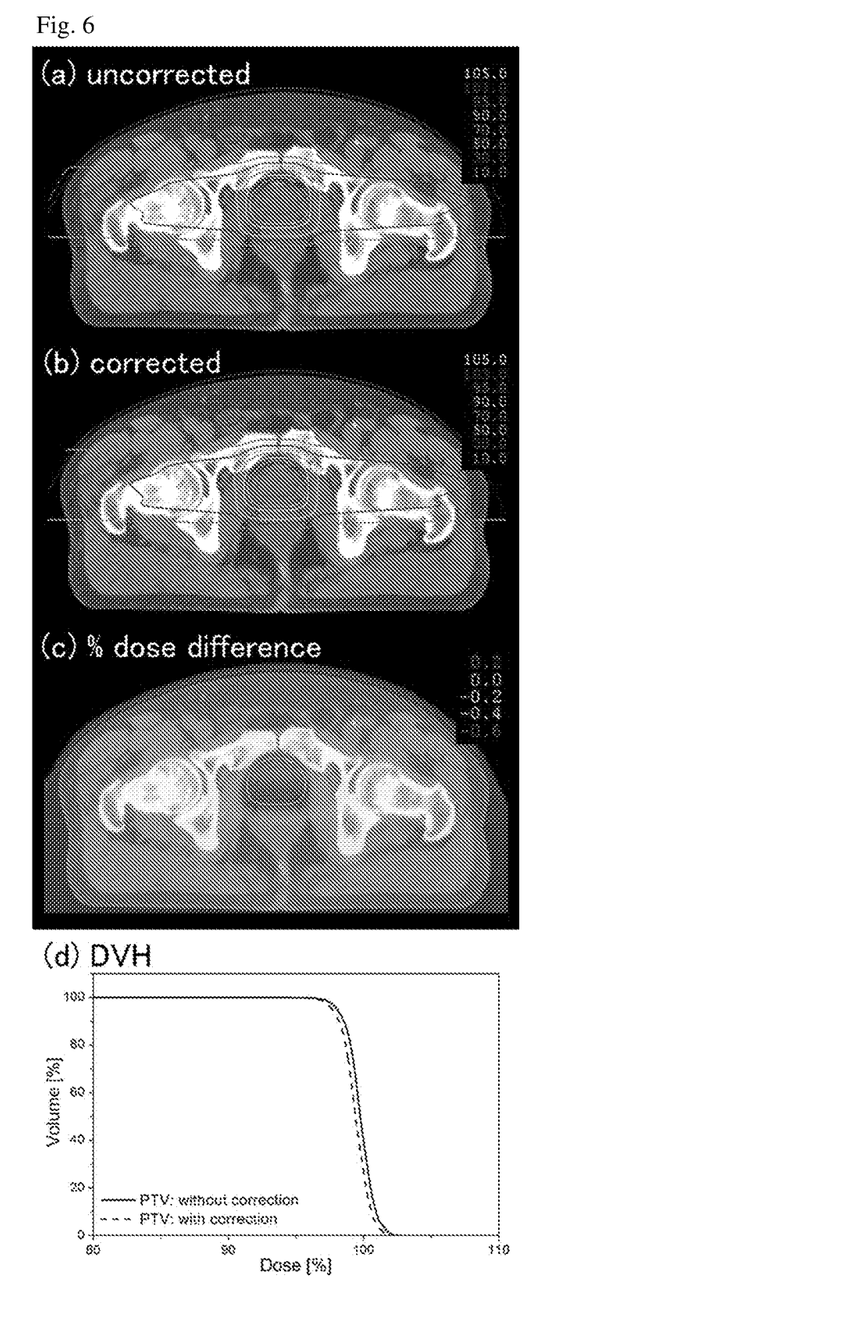
FIG. 6 is a combination of an image diagram illustrating a series of conversion, and a histogram.

FIG. 6 is a combination of an image diagram illustrating a series of conversion, and a histogram. FIG. 6(a) shows an image of uncorrected dose distribution. FIG. 6(b) shows an image of corrected dose distribution. FIG. 6(c) shows an image illustrating a dose difference between the dose before correction (uncorrected) and the dose after correction. FIG. 6(d) is a dose volume histogram having a vertical axis representing the volume, and a horizontal axis representing the dose. Thus, generation of a nuclear reaction effective density image from CT values to apply the correction described above enables a high accuracy particle beam irradiation plan to be developed.

One embodiment of the present invention will be described below with reference to the drawings.

Example 1

Figure 7:
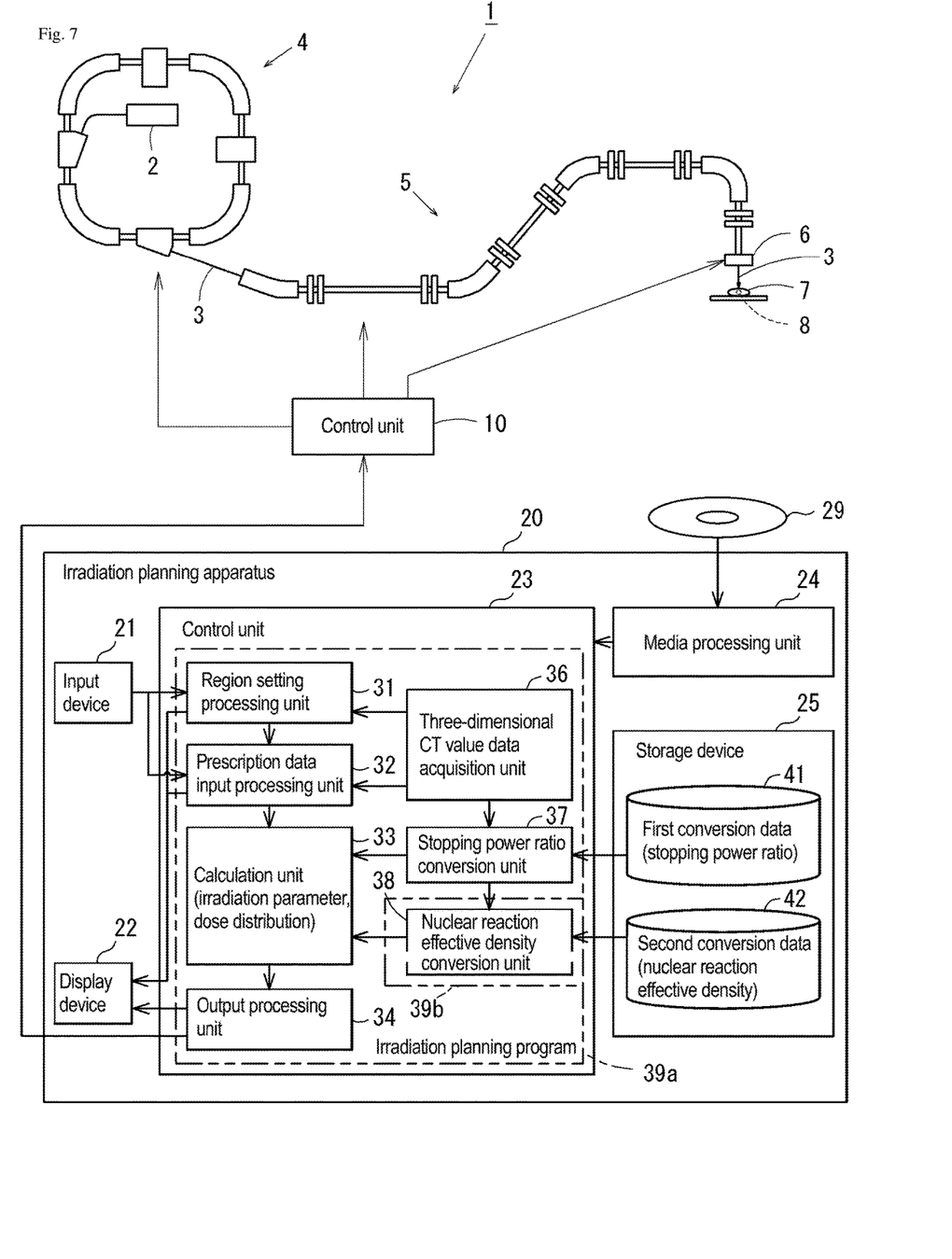
FIG. 7 is an illustrative diagram illustrating an overall configuration of a particle beam irradiation system.

FIG. 7 is an illustrative diagram illustrating an overall configuration of a particle beam irradiation system 1 according to a first embodiment of the present invention.

The particle beam irradiation system 1 includes an accelerator 4 that accelerates and outputs a charged particle beam 3 emitted from an ion source 2; a beam transport system 5 that transports the charged particle beam 3 output from the accelerator 4; an irradiation apparatus (scanning irradiation apparatus) 6 that irradiates a target region 8 (e.g., a tumor region), which is an irradiated object of a patient 7, with the charged particle beam 3 that has passed through the beam transport system 5; a control unit 10 that controls the particle beam irradiation system 1; and an irradiation planning apparatus 20, which is a computer that determines an irradiation parameter of the particle beam irradiation system 1. This example assumes that a carbon ion beam is used as the charged particle beam 3 emitted from the ion source 2, but the charged particle beam 3 is not limited thereto, and the present invention can be applied to particle beam irradiation systems 1 that emit various charged particle beams (including charged heavy particle beams).

The accelerator 4 is configured to adjust the intensity of the charged particle beam 3.

The irradiation apparatus 6 includes a scanning magnet (not shown) that deflects the charged particle beam 3 in an X-Y direction forming a plane perpendicular to the beam propagation direction (z-direction); a dose monitor (not shown) that monitors the position of the charged particle beam 3; and a range shifter (not shown) that adjusts the stopping location of the charged particle beam 3 in the Z-direction. The irradiation apparatus 6 is configured to scan the charged particle beam 3 along a scanning trajectory for the target region 8.

The control unit 10 is configured to control the intensity of the charged particle beam 3 from the accelerator 4, alignment adjustment of the charged particle beam 3 in the beam transport system 5, scanning performed by the scanning magnet (not shown) of the irradiation apparatus 6, the beam stopping location embodied by the range shifter (not shown), etc.

The irradiation planning apparatus 20 includes an input device 21 including a keyboard, a mouse, etc.; a display device 22 including a liquid crystal display, a CRT display, or the like; a control unit 23 including a CPU, a ROM, and a RAM; a media processing unit 24 including a disk drive and/or the like that reads and writes data from and to a storage medium 29, such as a CD-ROM or a DVD-ROM; and a storage device 25 including a hard disk or the like.

The control unit 23 reads an irradiation planning program 39a and an irradiation plan correction program 39b stored in the storage device 25. The control unit 23 functions as a region setting processing unit 31, as a prescription data input processing unit 32, as a calculation unit 33, as an output processing unit 34, as a three-dimensional CT value data acquisition unit 36, as a stopping power ratio conversion unit 37, and as a nuclear reaction effective density conversion unit 38.

The storage unit 25 stores first conversion data 41 for converting three-dimensional CT value data (three-dimensional scanned data) into a stopping power ratio, and second conversion data 42 for converting this stopping power ratio into a nuclear reaction effective density. The first conversion data 41 is data of a conversion table for converting CT values into a stopping power ratio according to a conventional technology. The second conversion data 42 is data of a conversion table for converting the stopping power ratio into a nuclear reaction effective density according to the present invention. The attenuation correction factor $\varphi_w^P(z)$ can be determined using Eqs. 2 to 4 described above from three-dimensional distributions of the stopping power ratio and of the nuclear reaction effective density obtained by the respective conversions.

The irradiation planning apparatus 20 configured as described above includes functional units that each operate as described below according to the irradiation planning program 39a and the irradiation plan correction program 39b.

First, the three-dimensional CT value data acquisition unit 36 obtains three-dimensional CT value data of an irradiated object (patient) from another CT apparatus. That is, values of an effective linear attenuation coefficient for an X-ray at respective three-dimensional locations of the irradiated object are obtained as three-dimensional CT value data.

The region setting processing unit 31 causes the display device 22 to display the three-dimensional CT value data as an image, and receives region specification data (specification data of the target region 8) that a planner inputs using the input device 21.

The prescription data input processing unit 32 causes the display device 22 to display a prescription input window, and receives prescription data that a planner inputs using the input device 21. This prescription data is data representing the irradiated location and the irradiation level of the particle beam at each coordinate point of the three-dimensional CT value data. It should be noted that this prescription data may include prescription data of multiple types of particle beam, and may thus include irradiated location and irradiation level data for each of the multiple types of particle beam, as well as data indicating the type of the particle beam (e.g., atomic nuclei of carbon, atomic nuclei of hydrogen, or the like).

The stopping power ratio conversion unit 37 uses the previously prepared first conversion data (conversion table) to convert the three-dimensional CT value data into the stopping power ratio $\rho_S$ at each of the three-dimensional locations as is performed in a standard particle beam irradiation planning apparatus. This conversion process provides stopping power ratio data, which describes a three-dimensional distribution of the stopping power ratio $\rho_S$. The conversion into the stopping power ratio data can be performed using a conventional technology of conversion that uses a previously prepared conversion table.

The nuclear reaction effective density conversion unit 38 converts the stopping power ratio data into the nuclear reaction effective density $\rho_N$ at each of the three-dimensional locations using the second conversion data that represent correlation between the stopping power ratio $\rho_S$ and the nuclear reaction effective density $\rho_N$ in human tissues, and thus derives a three-dimensional distribution of the nuclear reaction effective density $\rho_N$. This conversion process provides nuclear reaction effective density data, which describes a three-dimensional distribution of the nuclear reaction effective density. Thus, dose calculation for a body is performed by correcting, depending on depth, a dose distribution according to Eq. 5 using the attenuation correction factor $\varphi_w^P(z)$ obtained by Eqs. 2 to 4 shown above, and then applying the corrected dose distribution, instead of simply applying the dose distribution obtained by the measurement in water.

The calculation unit 33 receives the prescription data, the stopping power ratio data, and the nuclear reaction effective density data, and on the basis of these data, calculates irradiation parameters and a dose distribution. That is, in order to irradiate the irradiated location indicated by the prescription data at the irradiation level indicated by the prescription data, the intensity (number of particles) of the particle beam to be emitted from the particle beam irradiation system 1 is back-calculated using both the stopping power ratio data and the nuclear reaction effective density data, and then irradiation parameters of the particle beam emitted from the particle beam irradiation system 1 are calculated. In addition, the calculation unit 33 calculates the dose distribution when an irradiated object is irradiated with a particle beam having the irradiation parameters calculated.

The output processing unit 34 outputs the irradiation parameters and the dose distribution calculated to the display device 22, and allows them to be displayed thereon. In addition, the output processing unit 34 transmits the irradiation parameters and the dose distribution to the control unit 10, which controls the particle beam irradiation system 1.

The irradiation planning apparatus 20 described above enables the particle beam irradiation system 1 to emit a high accuracy beam by using irradiation parameters corrected with high accuracy depending on the irradiated object, instead of using irradiation parameters as planned, approximated by those of water. The beam irradiation may be any appropriate irradiation including, for example, spot beam irradiation (its dose distribution is the sum of those of the spot beams) using a scanning irradiation method, which provides irradiation having a uniform dose distribution, to a target region.

The second conversion data 42 is used for correction in association with the nuclear reaction effective density in addition to the correction in association with the stopping power ratio, and accordingly, is directly introduceable into irradiation planning apparatuses 20 of various existing particle beam irradiation systems 1 for practical use. In more detail, CT values are specific to the CT apparatus and imaging environment, and thus, the conversion table for converting these CT values into stopping power ratio values are also specific to the CT apparatus and imaging environment. Thus, performing correction of the nuclear reaction effective density directly from CT values requires generation of a conversion table for each CT apparatus and for each imaging environment. Meanwhile, an existing particle beam irradiation system 1 includes a conversion table for conversion into stopping power ratio values for a CT apparatus already installed and for imaging environment. Accordingly, use of this conversion table can eliminate the need for apparatus- and environment-specific settings. That is, once one second conversion data 42 is generated, correction can be performed using the nuclear reaction effective density determined using the second conversion data 42 from the stopping power ratio calculated using an individually adjusted conversion table, whatever CT apparatus and whatever imaging environment may be used. The standardization of the second conversion data 42 for performing correction in such a manner can, as well, prevent incorrect data from being used during installation, and can therefore safely provide development of a high accuracy irradiation plan.

Moreover, instead of simply applying the dose distribution obtained by a measurement in water (Eq. 1 described above) to calculation of a dose distribution in a body, correcting the dose distribution depending on the degree of the probability of nuclear reaction in the material through which the beam passes, and then applying the corrected dose distribution, enables the dose error introduced by nuclear reaction to be simply corrected.

Furthermore, this irradiation planning apparatus 20 can accurately reflect an effect of nuclear reaction induced by incident particles in the body during dose distribution calculation in particle beam irradiation planning. This enables more accurate dose distribution calculation in consideration of body tissues. In addition, this method is easy to use, takes advantage of universal nature of human tissues, and is usable in any irradiation planning apparatus. Accordingly, this method may become a standard, in the future, among dose calculation algorithms for particle beam irradiation planning that involves a carbon ion beam.

Example 2

Figure 8:
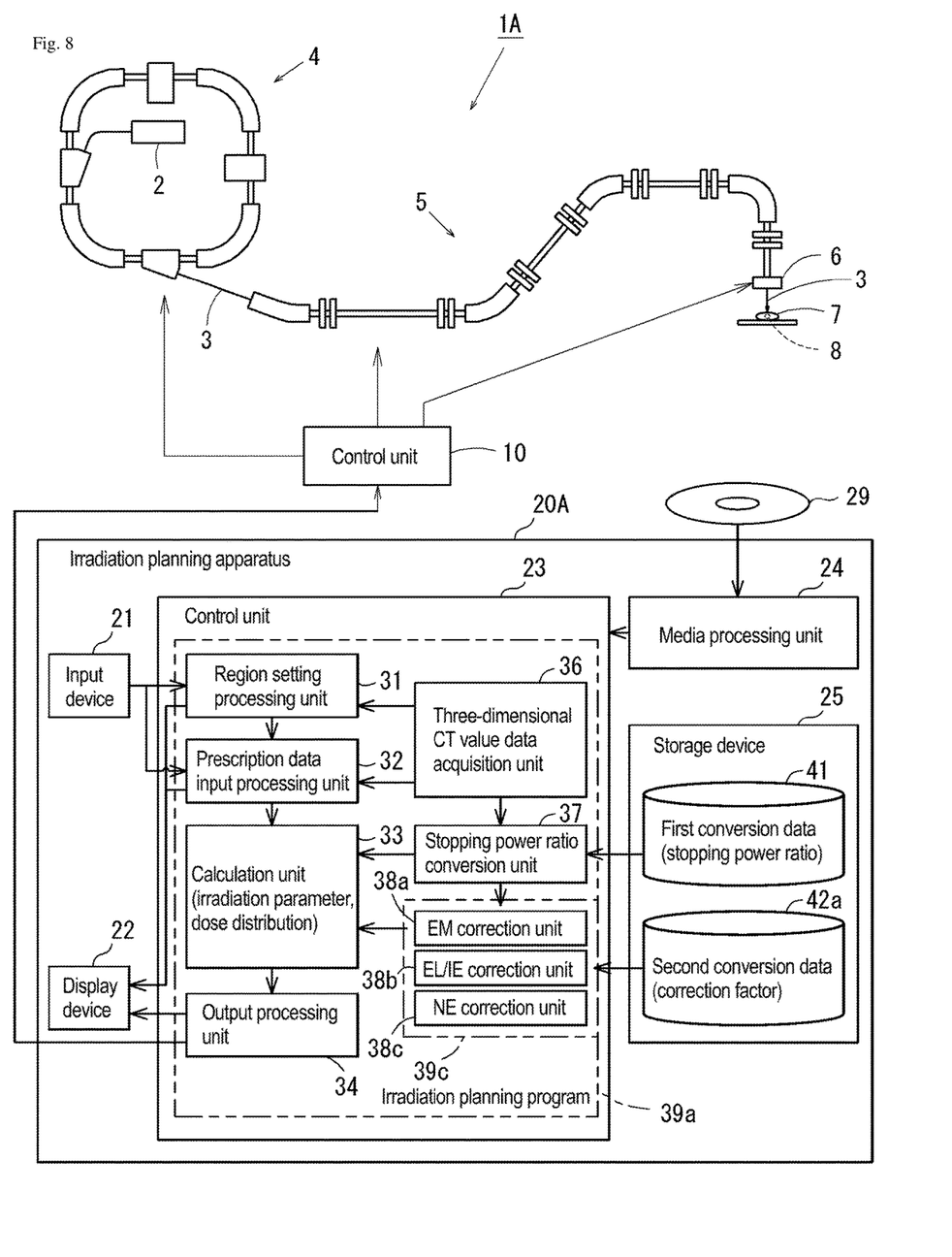
FIG. 8 is an illustrative diagram illustrating an overall configuration of a particle beam irradiation system 1A according to a second embodiment.

FIG. 8 is an illustrative diagram illustrating an overall configuration of a particle beam irradiation system 1A according to a second embodiment of the present invention. The second embodiment differs from the first embodiment in the configuration in that the nuclear reaction effective density conversion unit 38 (see FIG. 7) is replaced with an EM correction unit 38a, an EL/IE correction unit 38b, and an NE correction unit 38c; the irradiation plan correction program 39b (see FIG. 7) is replaced with an irradiation plan correction program 39c; and the second conversion data 42 is replaced with second conversion data 42a.

The EM correction unit 38a, the ELITE correction unit 38b, and the NE correction unit 38c receive stopping power ratio data from the stopping power ratio conversion unit 37, and receive the correction factors A'/A, Y'/Y, and $\gamma'/\gamma$ from the second conversion data 42a, and perform correction accordingly.

The EM correction unit 38a is a unit that performs correction in association with electromagnetic interaction (EM). The EL/IE correction unit 38b is a unit that performs correction in association with elastic interaction (EL) and inelastic interaction (IE). The NE correction unit 38c is a unit that performs correction in association with nuclear reaction (NE).

The irradiation plan correction program 39c causes each of the functional units of the irradiation planning apparatus 20A to operate in a similar manner to those of the first embodiment. In particular, in this second embodiment, the correction of irradiation plan is performed by the EM correction unit 38a, the EL/IE correction unit 38b, and the NE correction unit 38c, using Eq. 8 described above and second conversion data 42a.

The second conversion data 42a includes the correction factors A'/A, Y'/Y, and $\gamma'/\gamma$ of each tissue.

The other portions of the configuration and operation are identical to those of the first embodiment, and therefore, like reference characters indicate the same or equivalent components, and the explanation thereof will be omitted.

According to the configuration and operation described above, the particle beam irradiation system 1A of the second embodiment can emit a high accuracy beam by using irradiation parameters corrected with high accuracy depending on the irradiated object, instead of using irradiation parameters as planned, approximated by those of water. The beam irradiation may be any appropriate irradiation including, for example, spot beam irradiation (its dose distribution is the sum of those of the spot beams) using a scanning irradiation method, which provides irradiation having a uniform dose distribution, to a target region.

The second conversion data 42a enables the correction factors to be derived from the stopping power ratio, and accordingly, is directly introduceable into the irradiation planning apparatus 20A of various existing particle beam irradiation system 1A for practical use. In more detail, CT values are specific to the CT apparatus and imaging environment, and thus, the conversion table for converting these CT values into stopping power ratio values are also specific to the CT apparatus and imaging environment. Thus, performing correction directly from CT values requires generation of a conversion table for each CT apparatus and for each imaging environment. Meanwhile, an existing particle beam irradiation system 1A includes a conversion table (conversion table for converting attenuation of X-ray into stopping perlation of the particle beam) for conversion into stopping power ratio values for a CT apparatus already installed and for imaging environment. Accordingly, use of this conversion table can eliminate the need for apparatus- and environment-specific settings. That is, once one second conversion data 42a is generated, the stopping power ratio values calculated using an individually adjusted conversion table can be converted into distributions of correction factors in association with electromagnetic interaction (EM), elastic interaction (EL), inelastic interaction (IE), and nuclear reaction (NE) using the second conversion data 42a, and thus correction can be provided in consideration of differences in the contributions of these types of interaction between in a material of interest and in water, whatever CT apparatus and whatever imaging environment may be used. The standardization of the second conversion data 42a for performing correction in such a manner can, as well, prevent incorrect data from being used during installation, and can therefore safely provide development of a high accuracy irradiation plan.

Moreover, instead of simply applying the dose distribution obtained by a measurement in water (Eq. 1 described in relation to the first embodiment) to calculation of a dose distribution in a body, correcting the dose distribution depending on the degree of the probability of nuclear reaction in the material through which the beam passes, and then applying the corrected dose distribution, enables the dose error introduced by nuclear reaction to be simply corrected.

Furthermore, this irradiation planning apparatus 20A can accurately reflect an effect of nuclear reaction induced by incident particles in the body during dose distribution calculation in particle beam irradiation planning. This enables more accurate dose distribution calculation in consideration of body tissues. In addition, this method is easy to use, takes advantage of universal nature of human tissues, and is usable in any irradiation planning apparatus. Accordingly, this method may become a standard, in the future, among dose calculation algorithms for particle beam irradiation planning that involves a proton beam.

The present invention corresponds to the embodiments as follows: the particle beam of the present invention corresponds to the charged particle beam 3 of the embodiments; and similarly, the irradiated object corresponds to the patient 7;
the region corresponds to the target region 8;
the irradiation planning apparatus and the computer correspond to the irradiation planning apparatus 20;
the prescription data acquisition unit corresponds to the prescription data input processing unit 32;
the dose distribution calculation unit corresponds to the calculation unit 33;
the three-dimensional scanned data acquisition unit corresponds to the three-dimensional CT value data acquisition unit 36;
the reaction-physical-quantity distribution data generation unit corresponds to the stopping power ratio conversion unit 37 and the nuclear reaction effective density conversion unit 38;
the stopping power ratio correction processing unit corresponds to the stopping power ratio conversion unit 37;
the irradiated object material correction processing unit corresponds to the nuclear reaction effective density conversion unit 38, the EM correction unit 38a, the EL/IE correction unit 38b, and the NE correction unit 38c;
the nuclear reaction effective density correction processing unit corresponds to the nuclear reaction effective density conversion unit 38;
the particle beam action correction processing unit corresponds to the EM correction unit 38a, the ELITE correction unit 38b, and the NE correction unit 38c;
the reaction physical quantity distribution data corresponds to the first conversion data 41 and the second conversion data 42, 42a;
the three-dimensional stopping power ratio data corresponds to the first conversion data 41;
the three-dimensional nuclear reaction effective density data corresponds to the second conversion data 42; and
the component(s) correspond(s) to the first component, the second component, and/or the third component;
but the correspondences are not limited to these.

It should be noted that the atomic numbers of respective components in relation to correction in the example of the first embodiment described above are specifically directed to carbon ion therapy using carbon whose atomic number is 6; however, the type of therapy is not limited thereto, and the atomic numbers of the components may be in any appropriate range if other nuclear species having a different atomic number is used.

In addition, in the second embodiment, the correction process is performed using Eq. 8 such that the three components in association with "EM," "EL/IE," and "NE" are each corrected, and are then summed up. However, the correction process is not limited thereto, and thus the dose distribution may have any appropriate combination of components, such as one having two components in association with "EM+EL/IE" and "NE," one having four components in association with "EM," "EL," "IE," and "NE," etc. These cases can also achieve development of an irradiation plan depending on the irradiated object, including irradiation parameters having improved accuracy as compared with irradiation parameters as planned, approximated by those of water.

Furthermore, the stopping power ratio correction processing unit (the stopping power ratio conversion unit 37) and the irradiated object material correction processing unit (the nuclear reaction effective density conversion unit 38, the EM correction unit 38a, the EL/IE correction unit 38b, and the NE correction unit 38c) need only to be conceptually separated into two series in terms of calculation. Therefore, the calculation may be performed such that these two series of correction processes are executed at one time in one operation.

INDUSTRIAL APPLICABILITY

The present invention is usable in a technology of therapy using particle beam irradiation.

REFERENCE SIGNS LIST

3: Charged particle beam
7: Patient
8: Target region
20, 20A: Irradiation planning apparatus
32: Prescription data input processing unit
33: Calculation unit
36: Three-dimensional scanned data acquisition unit
37: Stopping power ratio conversion unit
38: Nuclear reaction effective density conversion unit
38a: EM correction unit 38a
38b: EL/IE correction unit 38b
38c: NE correction unit 38c
41: First conversion data
42, 42a: Second conversion data

The invention claimed is:

1. An irradiation planning apparatus for developing an irradiation plan involving a particle beam, the apparatus comprising:

a CT apparatus configured to acquire three-dimensional scanned data generated by three-dimensional scanning of an object to be irradiated by the particle beam, the three-dimensional scanning utilizing radiation different from the particle beam;

a data input configured to acquire prescription data indicative of a position and a volume of a region of the object to be irradiated with the particle beam;

a control unit configured to:
  generate reaction physical quantity distribution data on the basis of the three-dimensional scanned data, the reaction physical quantity distribution data being indicative of a distribution of a physical quantity indicative of capability of a material of the object to react with the particle beam, and
  calculate a dose distribution for the particle beam on the basis of the prescription data and the reaction physical quantity distribution data, wherein generating the reaction physical quantity distribution data includes:
    the control unit generating three-dimensional stopping power ratio data by converting each value in the three-dimensional scanned data into a respective stopping power ratio using a predetermined conversion table, the stopping power ratio being a physical quantity indicative of capability of a material to decelerate incident particles relative to a corresponding capability of water, and the three-dimensional stopping power ratio data including a distribution of the stopping power ratios of the object, and the control unit converting the three-dimensional stopping power ratio data into a nuclear reaction effective density data, the nuclear reaction effective density being a physical quantity indicative of a likelihood of spalling incident particles of a material relative to a corresponding likelihood for water, and calculating the dose distribution includes the control unit determining, from the nuclear reaction effective density data, a correction factor representing a difference between the capabilities of water and the material of the object to react with the particle beam, and performing correction, depending on depth, of a depth dose distribution of the particle beam using the correction factor.

2. The irradiation planning apparatus according to claim 1, wherein the control unit is configured to separate the depth dose distribution of the particle beam into components according to an atomic number or according to interaction of the particle beam, and perform correction of the depth dose distribution for each of the components.

3. The irradiation planning apparatus according to claim 2, wherein converting the three-dimensional stopping power ratio data into a nuclear reaction effective density includes generating three-dimensional nuclear reaction effective density data, and performing correction includes separating the depth dose distribution of the particle beam into components according to an atomic number, and correcting the depth dose distribution by separating the components into a component to which the correction factor is applied and a component to which the correction factor is not applied.

4. The irradiation planning apparatus according to claim 3, wherein the control unit classifies:
  a component in association with data atomic numbers from 3 to 5 as the component to which the correction factor is not applied,
  a component in association with an atomic number of 6 as a component to be multiplied by an attenuation correction factor determined from a change in a particle beam fluence, and
  a component in association with an atomic number from 1 to 2 as a component to be multiplied by an inverse of the attenuation correction factor.

5. The irradiation planning apparatus according to claim 2, wherein the control unit is configured to separate the depth dose distribution of the particle beam at least into a component in association with electromagnetic interaction and a component in association with nuclear reaction, and perform correction using the correction factor for each of the components separated.

6. The irradiation planning apparatus according to claim 5, wherein the control unit is configured to separate the depth dose distribution of the particle beam into three components, which are the component in association with electromagnetic interaction, the component in association with nuclear reaction, and a component in association with elastic interaction and inelastic interaction, perform correction using the correction factor for each of the components separated, and sum up the corrected values.

7. A non-transitory storage medium, comprising:

an irradiation planning program stored on the non-transitory storage medium, the irradiation planning program when read by a processor of a control unit causes the control unit to:
  acquire three-dimensional scanned data generated by a CT apparatus three-dimensional scanning an object to be irradiated by a particle beam, the three-dimension scanning utilizing radiation different from the particle beam;
  a data input to acquire prescription data indicative of a position and a volume of a region of the object to be irradiated with the particle beam,
  generate reaction physical quantity distribution data on the basis of the three-dimensional scanned data, the reaction physical quantity distribution data being indicative of a distribution of a physical quantity indicative of capability of a material of the object to react with the particle beam, and
  calculate a dose distribution on the basis of the prescription data and the reaction physical quantity distribution data,
wherein generating the reaction physical quantity distribution data includes:
  the control unit generating three-dimensional stopping power ratio data by converting each value in the three-dimensional scanned data into a respective stopping power ratio using a predetermined conversion table, the stopping power ratio being a physical quantity indicative of capability of material to decelerate incident particles relative to a corresponding capability of water, and the three-dimensional stopping power ratio data including a distribution of the stopping power ratios of the object, and
  the control unit converting the three-dimensional stopping power ratio data into a nuclear reaction effective density data, the nuclear reaction effective density being a physical quantity indicative of a likelihood of spalling incident particles of a material relative to a corresponding likelihood for water, and
calculating the dose distribution includes the control unit determining, from the nuclear reaction effective density data, a correction factor representing a difference between the capabilities of water and the material of the object material to reacting with the particle beam, and performing correction, depending on depth, of a depth dose distribution of the particle beam using the correction factor.

8. A non-transitory storage medium, comprising:

an irradiation plan correction program stored on the non-transitory storage medium, the irradiation planning program when read by a processor of a control unit causes the control unit to:
  generate three-dimensional stopping power ratio data by converting each value in three-dimensional scanned data into a respective stopping power ratio using a predetermined conversion table, the stopping power ratio being a physical quantity indicative of capability of a material to decelerate incident particles relative to a corresponding capability of water, and the three-dimensional stopping power ratio data including a distribution of the stopping power ratios of the object,
  convert the three-dimensional stopping power ratio data into a nuclear reaction effective density data, the nuclear reaction effective density being a physical quantity indicative of a likelihood of spalling incident particles of a material relative to a corresponding likelihood for water, and determine, from the nuclear reaction effective density data, a correction factor representing a difference between the capabilities of water and material of the object to react with the particle beam, and perform correction, depending on depth, of a depth dose distribution of a particle beam using the correction factor.

9. A method of irradiating an object with a particle beam, the method comprising:

acquiring three-dimensional scanned data of the object to be irradiated by the particle beam, the three-dimensional scanning utilizing radiation different from the particle beam;

converting each value in the three-dimensional scanned data into a respective stopping power ratio using a predetermined conversion table to generate three-dimensional stopping power ratio data, the stopping power ratio being a physical quantity indicative of capability of a material to decelerate incident particles relative to a corresponding capability of water, and the three-dimensional stopping power ratio data including a distribution of the stopping power ratios of the object;

converting the three-dimensional stopping power ratio data into a nuclear reaction effective density data, the nuclear reaction effective density being a physical quantity indicative of a likelihood of spalling incident particles of a material relative to a corresponding likelihood for water, determining, from the nuclear reaction effective density data, a correction factor representing a difference between the capabilities of water and the material of the object and performing correction, depending on depth, of a depth dose distribution of the particle beam using the correction factor; and irradiating the object with the particle beam utilizing the corrected depth dose distribution.

10. The method of claim 9, wherein acquiring three-dimensional scanned data of the object to be irradiated by the particle beam includes generating the three-dimensional scanned data by three-dimensionally scanning the object utilizing the radiation different from the particle beam.

11. A particle beam irradiation system, comprising:

a CT scanner configured to generate three-dimensional scanned data by three-dimensionally scanning an object to be irradiated by a particle beam, the three-dimensional scanning utilizing radiation different from the particle beam;

a data input configured to acquire prescription data indicative of a position and a volume of a region of the object to be irradiated with the particle beam;

a control unit configured to:

generate reaction physical quantity distribution data on the basis of the three-dimensional scanned data, the reaction physical quantity distribution data indicative of a distribution of a physical quantity indicative of capability of a material of the object—to react with the particle beam, and calculate a dose distribution for the particle beam on the basis of the prescription data and the reaction physical quantity distribution data; and the particle beam configured to irradiate the object according to the dose distribution, wherein generating the reaction physical quantity distribution data includes:

the control unit generating three-dimensional stopping power ratio data by converting each value in the three-dimensional scanned data into a respective stopping power ratio using a predetermined conversion table, the stopping power ratio being a physical quantity indicative of capability of a material to decelerate incident particles relative to a corresponding capability of water, the three-dimensional stopping power ratio data including a distribution of the stopping power ratios of the object, and the control unit converting the three-dimensional stopping power ratio data into a nuclear reaction effective density data, the nuclear reaction effective density being a physical quantity indicative of a likelihood of spalling incident particles of a material relative to a corresponding likelihood for water, and calculating the dose distribution includes the control unit determining, from the nuclear reaction effective density data, a correction factor representing a difference between the capabilities of water and the material of the object to react with the particle beam, and performing correction, depending on depth, of a depth dose distribution of the particle beam using the correction factor.

* * * * *